(12) United States Patent
Li

(10) Patent No.: US 8,239,011 B2
(45) Date of Patent: Aug. 7, 2012

(54) ATRIAL ARRHYTHMIA DETECTION AND DISCRIMINATION BASED ON INTRACARDIAC IMPEDANCE

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 141 days.

(21) Appl. No.: 12/757,125

(22) Filed: Apr. 9, 2010

(65) Prior Publication Data
US 2010/0280401 A1 Nov. 4, 2010

Related U.S. Application Data

(60) Provisional application No. 61/173,917, filed on Apr. 29, 2009.

(51) Int. Cl.
*A61B 5/02* (2006.01)
(52) U.S. Cl. ............ 600/518; 600/515; 600/547; 607/4; 607/14
(58) Field of Classification Search .................. 600/515, 600/518, 547; 607/4, 14
See application file for complete search history.

(56) References Cited

U.S. PATENT DOCUMENTS

| | | |
|---|---|---|
| 4,773,401 A | 9/1988 | Citak et al. |
| 5,249,699 A | 10/1993 | Williams |
| 5,370,667 A * | 12/1994 | Alt .................................. 607/19 |
| 5,591,215 A | 1/1997 | Greenhut et al. |
| 5,755,736 A | 5/1998 | Gillberg et al. |
| 5,759,196 A | 6/1998 | Hess et al. |
| 5,840,079 A | 11/1998 | Warman et al. |
| 5,968,079 A | 10/1999 | Warman et al. |
| 5,991,657 A | 11/1999 | Kim |
| 6,047,210 A | 4/2000 | Kim et al. |
| 6,052,620 A | 4/2000 | Gillberg et al. |
| 6,091,988 A | 7/2000 | Warman et al. |
| 6,249,699 B1 | 6/2001 | Kim |
| 6,272,380 B1 | 8/2001 | Warman et al. |
| 6,330,477 B1 | 12/2001 | Casavant |
| 6,434,424 B1 | 8/2002 | Igel et al. |
| 6,493,579 B1 | 12/2002 | Gilkerson et al. |

(Continued)

OTHER PUBLICATIONS

Schmidt, B., et al., "Atrial fibrillation reduces the atrial impedance amplitude during cardiac cycle: a novel detection algorithm to improve recognition of atrial fibrillation in pacemaker patients", *Europace*, 9(9), (2007), 812-816.

*Primary Examiner* — Niketa Patel
*Assistant Examiner* — William Levicky
(74) *Attorney, Agent, or Firm* — Schwegman, Lundberg & Woessner, P.A.

(57) ABSTRACT

An apparatus comprises an implantable impedance sensing circuit configured to sense an atrial impedance signal when coupled to a plurality of implantable electrodes, and an impedance signal analyzer circuit configured to detect a sudden change in a characteristic of the sensed atrial impedance signal that indicates atrial tachyarrhythmia. The impedance signal analyzer circuit classifies the atrial tachyarrhythmia indication as ST when the detected sudden change satisfies an ST threshold value of the characteristic, classifies the atrial tachyarrhythmia indication as AT when the detected sudden change satisfies an AT threshold value of the characteristic that is different from the ST threshold value, classifies the atrial tachyarrhythmia indication as AF when the detected sudden change satisfies an AF threshold value of the characteristic that is different from the ST and AT amplitude threshold values, and provides a classification of the tachyarrhythmia to a user or process.

25 Claims, 4 Drawing Sheets

U.S. PATENT DOCUMENTS

| | | |
|---|---|---|
| 6,584,350 B2 | 6/2003 | Kim et al. |
| 6,658,286 B2 | 12/2003 | Seim |
| 6,704,597 B1 | 3/2004 | Ware et al. |
| 6,829,504 B1 | 12/2004 | Chen et al. |
| 6,889,081 B2 | 5/2005 | Hsu |
| 7,050,852 B2 | 5/2006 | Zhu et al. |
| 7,058,448 B2 | 6/2006 | Noren |
| 7,076,300 B1 | 7/2006 | Kroll et al. |
| 7,110,811 B2 | 9/2006 | Wagner et al. |
| 7,142,918 B2 | 11/2006 | Stahmann et al. |
| 7,203,539 B2 | 4/2007 | Ware et al. |
| 7,209,785 B2 | 4/2007 | Kim et al. |
| 7,212,860 B2 | 5/2007 | Stahmann et al. |
| 7,228,176 B2 | 6/2007 | Smith et al. |
| 7,272,438 B2 | 9/2007 | Kroll et al. |
| 7,328,063 B2 | 2/2008 | Zhang et al. |
| 7,398,123 B1 | 7/2008 | Levine |
| 7,537,569 B2 | 5/2009 | Sarkar et al. |
| 7,580,740 B2 | 8/2009 | Kim et al. |
| 2006/0155201 A1* | 7/2006 | Schwartz et al. ............. 600/510 |
| 2007/0156058 A1* | 7/2007 | Faber et al. ................... 600/515 |
| 2007/0219456 A1 | 9/2007 | Thompson |
| 2007/0288062 A1 | 12/2007 | Stahmann et al. |
| 2008/0114258 A1 | 5/2008 | Zhang et al. |
| 2009/0054943 A1 | 2/2009 | Qu et al. |
| 2009/0163966 A1 | 6/2009 | Perschbacher et al. |
| 2009/0299425 A1 | 12/2009 | Kim et al. |
| 2009/0306486 A1 | 12/2009 | Li et al. |

* cited by examiner

ATRIAL ARRHYTHMIA DETECTION AND DISCRIMINATION BASED ON INTRACARDIAC IMPEDANCE

CROSS REFERENCE TO RELATED APPLICATION

Benefit of priority is hereby claimed to U.S. Provisional Patent Application Ser. No. 61/173,917, filed on Apr. 29, 2009, the specification of which is herein incorporated by reference in its entirety.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect abnormally rapid heart rate, or tachyarrhythmia. Some tachyarrhythmia is treated by delivering high-energy electrical shock therapy with the IMD.

Patients that use IMDs may be adversely affected by misinterpretations of signals sensed by the IMD sensing circuits. If an IMD incorrectly interprets a sensed signal as indicating tachyarrhythmia, the IMDs may inappropriately deliver shock therapy, causing patient discomfort. Atrial fibrillation (AF) is a form of tachyarrhythmia not typically treated with shock therapy. However, AF may be incorrectly interpreted as ventricular tachycardia (VT), which is often treated with shock therapy, causing incorrect identification of AF a leading cause of inappropriate therapy delivery. The rate of inappropriate deliveries has not been shown to be significantly different between single chamber CFM devices and multi-chamber CFM devices using existing AF detection algorithms. Thus, there is a need for improved sensing of events related to device recognition and classification of tachyarrhythmia.

Overview

This document relates generally to systems, devices, and methods for monitoring cardiac electrophysiological parameters of a patient or subject, and in particular for monitoring impedance in or near the atria of the heart. In example 1, an apparatus includes an implantable impedance sensing circuit configured to sense an atrial impedance signal when coupled to a plurality of implantable electrodes, and an impedance signal analyzer circuit configured to detect a sudden change in a characteristic of the sensed atrial impedance signal that indicates atrial tachyarrhythmia. The impedance signal analyzer circuit classifies the atrial tachyarrhythmia indication as sinus tachycardia (ST) when the detected sudden change satisfies an ST threshold value of the characteristic, classifies the atrial tachyarrhythmia indication as atrial tachycardia (AT) when the detected sudden change satisfies an AT threshold value of the characteristic that is different from the ST threshold value, classifies the atrial tachyarrhythmia indication as AF when the detected sudden change satisfies an AF threshold value of the characteristic that is different from the ST and AT amplitude threshold values, and provides a classification of the tachyarrhythmia to a user or process.

In example 2, the impedance signal analyzer circuit of example 1 is optionally configured to detect a sudden decrease in an amplitude of the sensed atrial impedance signal that is less than an amplitude threshold value, and classify the indication as ST, AT, or AF according to the detected decrease.

In example 3, the impedance signal analyzer circuit of any one or more of examples 1 and 2 is optionally configured to detect at least one of a sudden decrease in a calculated central tendency of the amplitude of the sensed atrial impedance signal, a sudden decrease in a baseline-to-peak amplitude of the atrial impedance signal, and a sudden decrease in a peak-to-peak amplitude of the atrial impedance signal.

In example 4, the impedance signal analyzer circuit of any one or more of examples 1-3 is optionally configured to detect a sudden change in an atrial depolarization rate or interval in the sensed atrial impedance signal that satisfies a specified rate or interval threshold value.

In example 5, the apparatus of any one or more of examples 1-4 optionally includes an implantable cardiac signal sensing circuit, communicatively coupled to the impedance signal analyzer circuit, configured to sense a cardiac signal associated with a cardiac action potential signal of the subject when coupled to a plurality of implantable electrodes, and the impedance signal analyzer circuit is optionally configured to detect the sudden change in the atrial depolarization rate or interval using both of the sensed atrial impedance signal and a sensed atrial action potential signal.

In example 6, the impedance signal analyzer circuit of any one or more of examples 1-5 is optionally configured to detect a sudden increase in variation of atrial depolarization rate or interval measured using the sensed atrial impedance signal.

In example 7, the impedance signal analyzer circuit of any one or more of examples 1-6 is optionally configured to detect a sudden decrease in a measure of regularity of the sensed atrial impedance signal that is less than a regularity measure threshold.

In example 8, the apparatus of any one or more of examples 1-7 optionally includes a memory, communicatively coupled to the impedance signal analyzer circuit, to store a template of morphology of an atrial impedance signal. The impedance signal analyzer circuit is optionally configured to compare the sensed atrial impedance signal to the stored morphology template, detect a change from the stored morphology template, and classify the detected tachyarrhythmia as one of ST, AT, or AF according to the comparison and to the sudden change in the characteristic.

In example 9, the apparatus of any one or more of examples 1-7 optionally includes a memory, communicatively coupled to the impedance signal analyzer circuit, to store a number of historical atrial impedance signal morphology templates and a current atrial impedance morphology template. The templates are indicative of a normal sinus rhythm (NSR). The impedance signal analyzer circuit is optionally configured to compare an atrial impedance signal sensed during NSR to the historical and current morphology templates, declare which morphology template is the current morphology template, and classify the detected tachyarrhythmia as one of ST, AT, or AF according to a comparison to the declared current morphology template.

In example 10, the impedance sensing circuit of any one or more of examples 1-9 is optionally configured to sense both the atrial impedance signal and a ventricular impedance signal of the subject. The impedance signal analyzer circuit is optionally configured to detect a sudden change, in a characteristic of the sensed ventricular impedance signal, that indicates ventricular tachycardia (VT), and provide an indication of atrial tachyarrhythmia and ventricular tachyarrhythmia to a user or process.

In example 11, the impedance sensing circuit of any one or more of examples 1-10 is optionally configured to sense a combined atrial and ventricular impedance signal of the subject. The impedance signal analyzer circuit is optionally configured to remove a ventricular component of the impedance signal to obtain the atrial component.

In example 12, the apparatus of any one or more of claims 1-11 optionally includes an implantable cardiac signal sensing circuit configured to sense a cardiac signal associated with a cardiac action potential signal of the subject when coupled to a plurality of implantable electrodes. The impedance signal analyzer circuit is optionally configured to classify the detected atrial tachyarrhythmia using the sensed atrial impedance signal and the sensed cardiac signal.

In example 13, the impedance signal analyzer circuit of any one or more of examples 1-12 is optionally configured to classify the tachyarrhythmia as AF or AT using the atrial impedance signal, detect a return to normal atrial impedance after detecting the AF or AT, determine a time duration of the AF or AT, calculate the AF or AT burden of the subject using the time duration, and provide the AF or AT burden calculation to a user or process.

In example 14, the implantable impedance sensing circuit of any one or more of examples 1-13 is optionally configured to be coupled to an implantable bipolar pair of impedance sensing electrodes and to sense a localized intra-atrial impedance signal using the implantable bipolar pair of impedance sensing electrodes.

In example 15, the apparatus of any one or more of examples 1-14 optionally includes an implantable housing and an electrode formed on the implantable housing. The implantable impedance sensing circuit is configured to sense a global atrial impedance signal using the electrode formed on the implantable housing.

In example 16, a method includes sensing an atrial impedance signal of a subject with an IMD, detecting a sudden change in a characteristic of the sensed atrial impedance signal that indicates atrial tachyarrhythmia, classifying the detected atrial tachyarrhythmia as ST when the sudden change in a characteristic of the atrial impedance signal satisfies an ST threshold value of the characteristic, classifying the detected atrial tachyarrhythmia as AT when the sudden change in the characteristic of the atrial impedance signal satisfies an AT threshold value of the characteristic that is different from the ST threshold value, classifying the detected atrial tachyarrhythmia as AF when the sudden change in the characteristic of the atrial impedance signal satisfies an AF threshold value of the characteristic that is different from the ST and AT amplitude threshold values, and providing a classification of the tachyarrhythmia to a user or process.

In example 17, the detecting a sudden change in a characteristic of the atrial impedance signal of example 16 optionally includes detecting a sudden decrease in an amplitude of the atrial impedance signal that is less than an amplitude threshold value, and the classifying optionally includes classifying the detected tachyarrhythmia as one of ST, AT, or AF according to the sudden decrease in amplitude.

In example 18, the detecting a sudden change in a characteristic of the atrial impedance signal of any one or more of examples 16 and 17 optionally includes detecting, using the atrial impedance signal, a sudden change in an atrial depolarization rate or interval that exceeds a rate threshold value or is less than a depolarization interval threshold value. The classifying optionally includes classifying the detected tachyarrhythmia as one of ST, AT, or AF according to the sudden change in the atrial depolarization rate or interval.

In example 19, the detecting the sudden change in a characteristic of the atrial impedance signal of any one or more of examples 16-18 optionally includes detecting a sudden decrease in a measure of regularity of the atrial impedance signal that is less than a regularity measure threshold. The classifying optionally includes classifying the detected tachyarrhythmia as one of ST, AT, or AF according to the sudden decrease in the measure of regularity.

In example 20, the detecting the sudden change in a characteristic of the atrial impedance signal of any one or more of examples 16-19 optionally includes detecting a sudden increase in a variation of atrial depolarization rate measured using the atrial impedance signal, and the classifying optionally includes classifying the detected tachyarrhythmia as one of ST, AT, or AF according to the sudden increase in the variation.

In example 21, the method of any one or more of examples 16-20 optionally includes storing a template of morphology of an atrial impedance signal, comparing the sensed atrial impedance signal to the stored morphology template, detecting the sudden change in a characteristic of the atrial impedance signal from the comparison to the stored morphology template, and classifying the detected tachyarrhythmia as one of ST, AT, or AF according to the comparison and to the sudden change in the characteristic.

In example 22, the storing the morphology template of an atrial impedance signal of example 21 optionally includes storing a number of historical atrial impedance signal morphology templates and a current atrial impedance morphology template. The templates are indicative of NSR. The method optionally includes comparing an atrial impedance signal sensed during NSR to the historical and current morphology templates, declaring which morphology template is the current morphology template, and classifying the detected tachyarrhythmia as one of ST, AT, or AF according to a comparison to the declared current morphology template.

In example 23, the method of any one or more of examples 16-22 optionally includes sensing a ventricular impedance signal of the subject with the IMD, detecting a sudden change, in a characteristic of the sensed ventricular impedance signal, that indicates ventricular tachycardia (VT), and providing an indication of atrial tachyarrhythmia and ventricular tachyarrhythmia to a user or process.

In example 24, the sensing an atrial impedance signal of any one or more of examples 16-24 optionally includes sensing a combined atrial and ventricular impedance signal, and removing a ventricular component of the impedance signal to obtain the atrial component.

In example 25, the classifying the detected tachyarrhythmia of any one or more of examples 16-24 optionally includes classifying the tachyarrhythmia as AF using the atrial impedance signal. The method optionally includes detecting a return to normal atrial impedance, determining the duration of the AF, calculating the AF burden of the subject using the time duration, and providing the AF burden calculation to a user or process.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

The present application discusses, among other things, devices, systems and methods for detecting and classifying cardiac arrhythmias using sensed atrial impedance. Atrial impedance measured with an implanted device can provide indications of changes in atrial wall motions, and changes in contractility or compliance of an atrium. Monitoring impedance can be used to detect relative changes in content of blood and tissue between impedance sensing electrodes.

Figure 1:
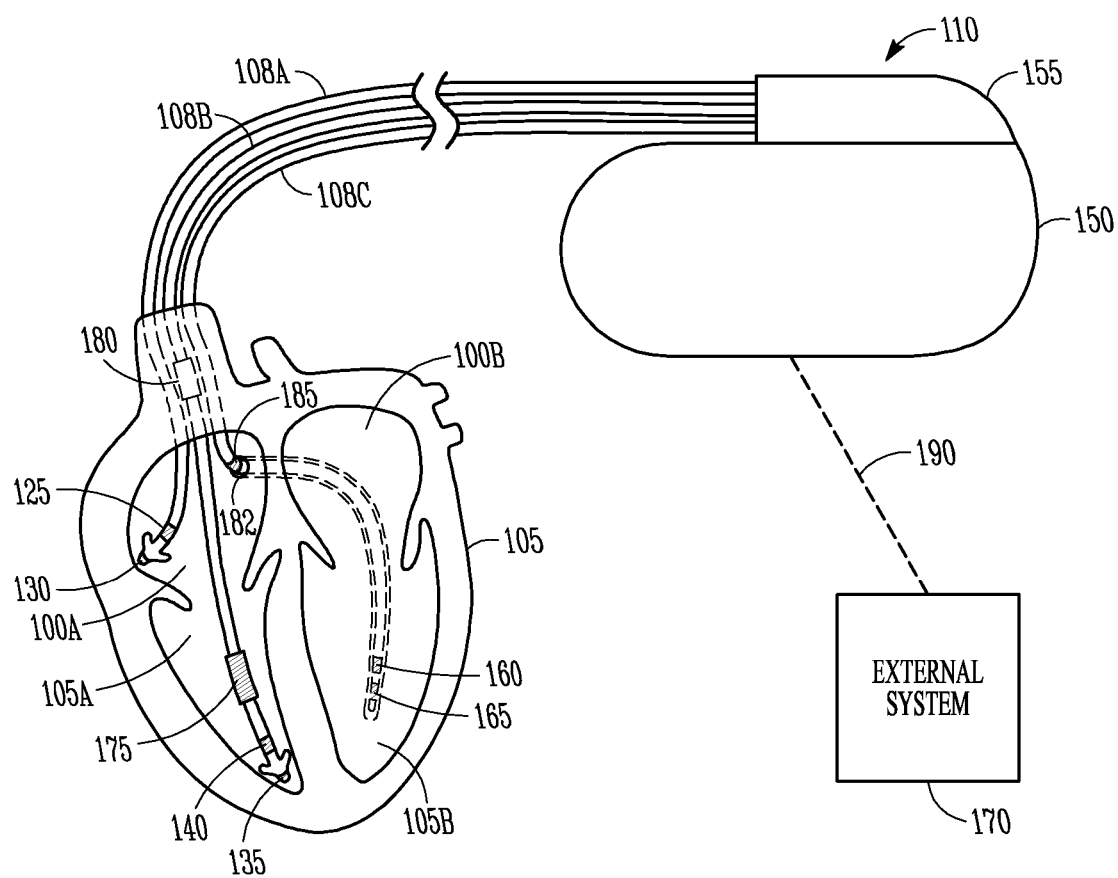
FIG. 1 is an illustration of portions of a system that uses an IMD.

FIG. 1 is an illustration of portions of a system that uses an IMD 110.

Examples of IMD 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Atrial lead 108A includes electrodes (electrical contacts, such as ring electrode 125 and tip electrode 130) disposed in an atrium 100A of heart 105 for sensing signals, or delivering pacing therapy, or both, to the atrium 100A.

Ventricular lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105.

The IMD 110 may include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein 120. The third cardiac lead 108C may include a ring electrode 185 positioned near the coronary sinus 182 (CS).

Lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrical contacts or "electrodes." Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the can 150, or a header 155, would be second vector.

To measure impedance, a specified excitation current is applied between electrodes and the voltage resulting from the excitation current is sensed between the same electrodes or different electrodes. The impedance is determined from the resulting voltage (e.g., by using Ohm's Law). For example, the excitation current could be delivered between ring electrodes 124, 140, and the voltage could be measured using either the same ring electrodes or measured between tip electrodes 130, 135. To avoid unintended stimulation of the heart, one or both of the magnitude and the pulse width of the applied excitation current is small. Atrial impedance can be measured between tip electrode 130 and ring electrode 125. These electrodes may be referred to as a bipolar pair of electrodes, and this impedance vector can be used to sense a localized intra-atrial impedance signal. Intra-atrial impedance will vary with the filling and emptying of blood in the chamber. Systems and methods to measure intra-cardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety.

Atrial impedance can also be measured between atrial tip electrode 130 or ring electrode 125 and an electrode formed on the can 150 or header 155. Such an arrangement of sensing electrodes is sometimes referred to as unipolar sensing. A unipolar impedance vector can be used to sense a global atrial impedance signal. A global impedance signal is a signal from a physiologic region of the subject (e.g., the thorax region) and may include multiple signal components. For example, the global impedance signal sensed between the ring electrode 125 and the can electrode may include an atrial impedance component and a respiration component.

The atrial component is extracted using signal processing techniques such as signal filtering. Left atrial (LA) impedance can be sensed between the CS electrode 185 and an electrode formed on the can 150 or header 155. Such an impedance vector would also provide a global impedance signal and may include multiple signal components.

Figure 2:
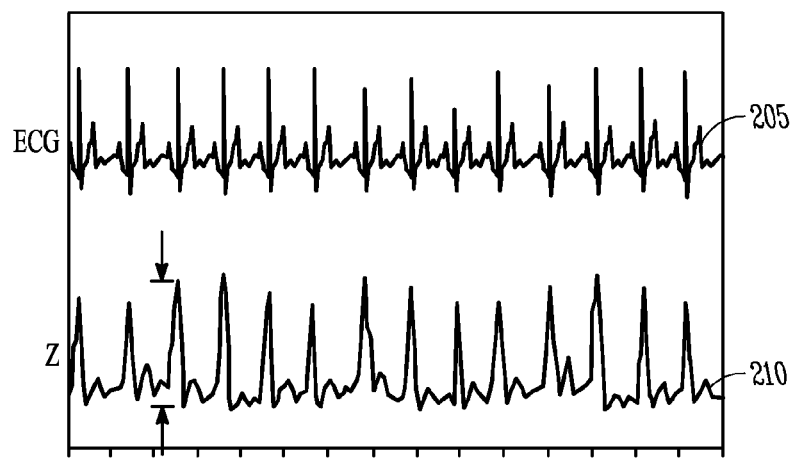
FIG. 2 is a graphical representation of an ECG signal and an atrial impedance signal.
Figure 3:
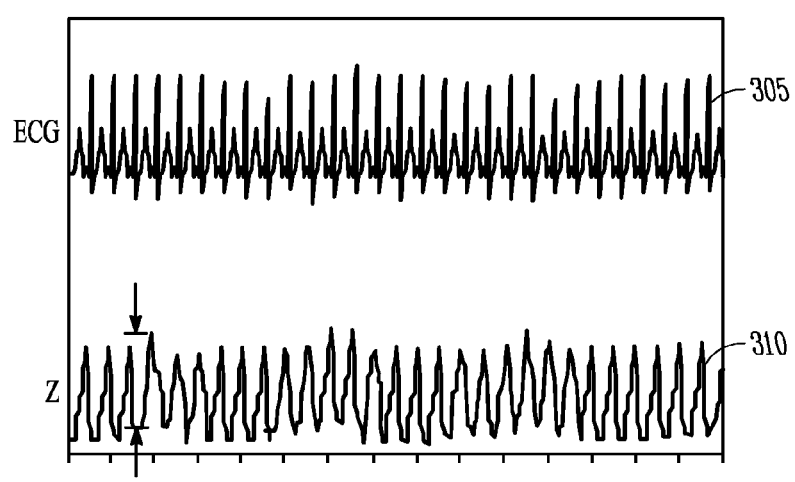
FIG. 3 is another graphical representation of an ECG signal and an atrial impedance signal.
Figure 4:
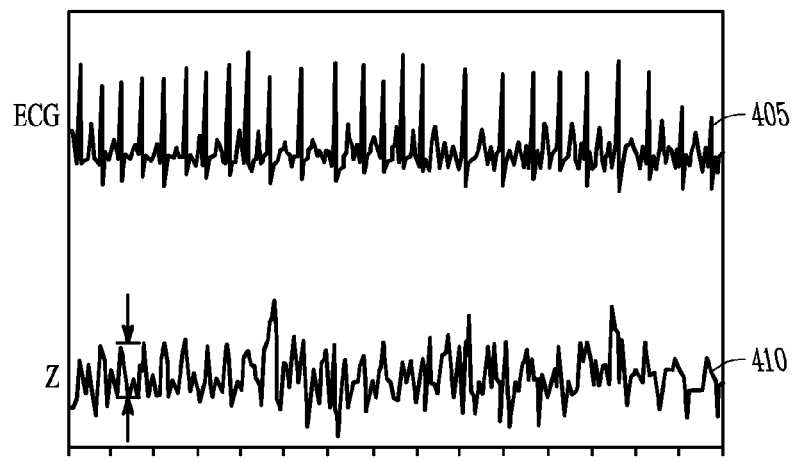
FIG. 4 is yet another graphical representation of an ECG signal and an atrial impedance signal.

FIGS. 2-4 are reproduced from Schmidt B, et al. Europace (2007) 9, 812-816. FIG. 2 is a graphical representation of an electrograph (ECG) signal 205 and an atrial impedance (Z) signal 210. The signals are representative of stable sinus rhythm. FIG. 3 is another graphical representation of an ECG signal 305 and an atrial impedance signal 310. The ECG signal 305 shows that the atrial depolarization rate increased. An increase in rate may be used to detect atrial tachycardia (AT), such as when the detected depolarization rate exceeds a detection rate threshold. Note that the atrial impedance signal still shows some regularity, but the amplitude of the impedance signal has decreased. This is due to less efficient emptying of the atrial chamber.

FIG. 4 is still another graphical representation of an ECG signal 405 and an atrial impedance signal 410. Here, the signals are representative of induced AF. The amplitude of the atrial impedance signal has decreased even lower than during AT and the signal is very irregular. The FIGS. show that sensed atrial impedance signals can be used to detect and classify atrial tachyarrhythmia.

Figure 5:
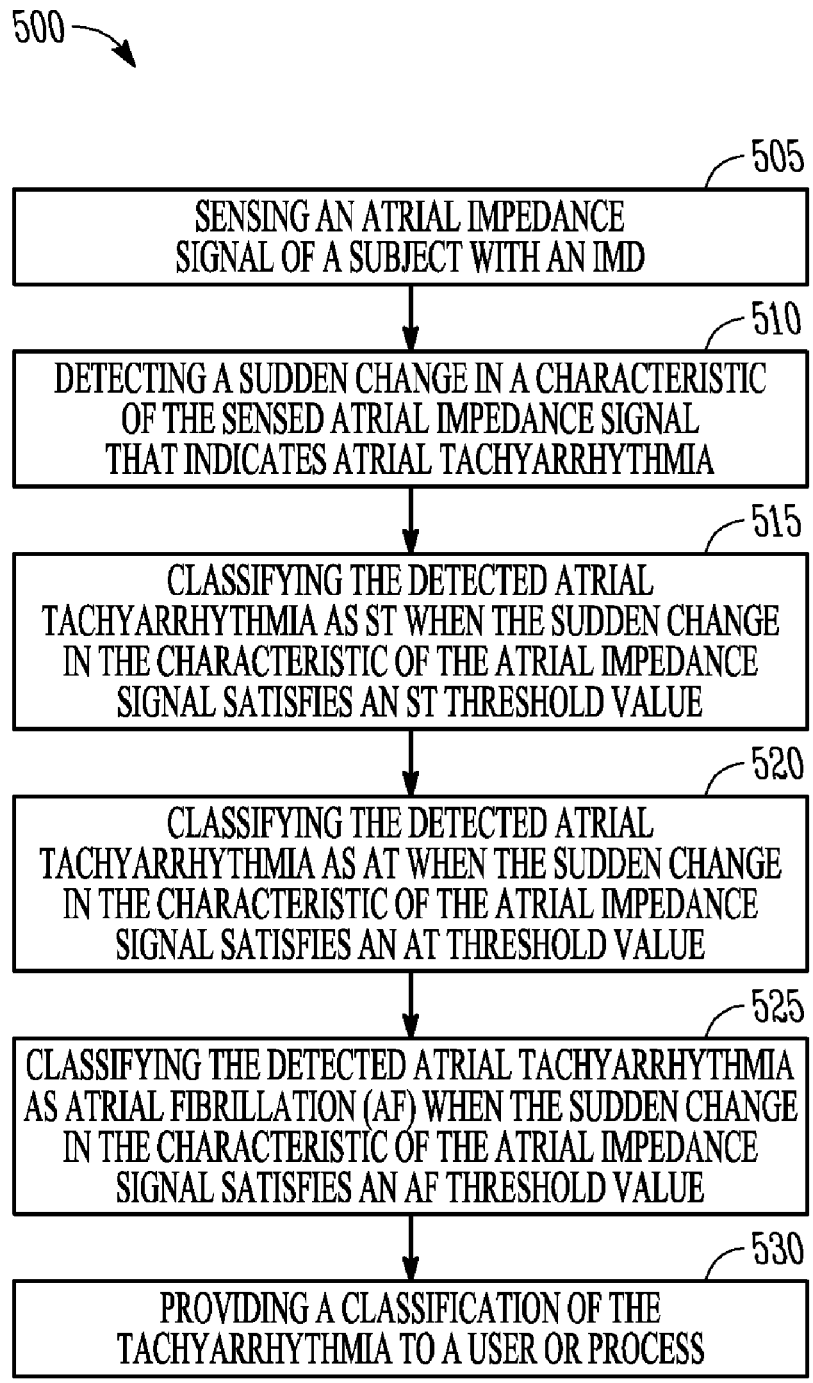
FIG. 5 shows a flow diagram of a method of detecting and classifying atrial tachyarrhythmia.

FIG. 5 shows a flow diagram of a method 500 of detecting and classifying atrial tachyarrhythmia. At block 505, an atrial impedance signal of a subject is sensed with an IMD. In some examples, the atrial impedance signal is an intra-atrial impedance signal. In some examples, the atrial impedance signal is measured between an electrode placed in or near the heart and an electrode on the can or header of the IMD.

At block 510, a sudden change is detected in a characteristic of the sensed atrial impedance signal that indicates atrial tachyarrhythmia. A change can be deemed to be sudden if a specified change occurs within a specified period of time, such as a specified number of cardiac cycles or a specified number of seconds, for example. In some examples, the sudden change includes a sudden decrease in the amplitude of the atrial impedance signal. The amplitude may be measured as, among other things, a baseline-to-peak amplitude, a peak-to-peak amplitude, or as a central tendency (e.g., as an average or median) of the amplitude. In some examples, the sudden change includes a sudden increase in the atrial depolarization rate (or conversely a sudden decrease in the depolarization interval) as measured in the atrial impedance signal. Sudden changes in other characteristics of the atrial impedance signal as described herein may also indicate atrial tachyarrhythmia.

At block 515, the detected atrial tachyarrhythmia is classified as sinus tachycardia (ST) when the sudden change in a characteristic of the atrial impedance signal satisfies an ST threshold value of the characteristic. For example, if the detected change includes a sudden decrease in amplitude, the tachyarrhythmia is classified as ST if the amplitude decreases below a specified ST amplitude detection threshold value. In another example, if the detected change includes a sudden increase in atrial depolarization rate or a sudden decrease in the atrial depolarization interval, the tachyarrhythmia is classified as ST if the rate increases above a specified ST rate detection threshold value or if the interval decreases below a specified ST interval detection threshold value.

At block 520, the detected atrial tachyarrhythmia is classified as AT when the sudden change in the characteristic of the atrial impedance signal satisfies an AT threshold value of the characteristic that is different from the ST threshold value. An AT arrhythmia will have a lower impedance amplitude than ST, which is a more regular rhythm and therefore is closer to a normal sinus rhythm. The rate of an AT arrhythmia will also typically be higher than in ST. Thus, the amplitude threshold for AT detection will be set lower than for ST detection. Similarly, the rate detection threshold for AT is higher than for ST, and the interval detection threshold for AT is less than the interval detection threshold for ST.

At block 525, the detected atrial tachyarrhythmia is classified as AF when the sudden change in the characteristic of the atrial impedance signal satisfies an AF threshold value of the characteristic that is different from the ST and AT amplitude threshold values. As is shown in FIGS. 2-4, the amplitude of the impedance signal during AF is lower than the amplitude during AT and the rate evident in the impedance signal is faster although much more irregular. The amplitude threshold for AF detection will be set lower than for either ST or AT detection. The rate detection threshold for AF is higher than for either ST or AT and the interval detection threshold for AF is less than the interval detection threshold for either ST or AT. The ST, AT, and AF thresholds may be programmable and determined by a physician for an individual patient or be programmed to a value based on a patient population.

At block 530, the method 500 includes providing a classification of the tachyarrhythmia to a user or process. In some examples, the classification may be used by the IMD to begin an anti-tachyarrhythmia treatment such as anti-tachycardia pacing (ATP) or delivery of an anti-tachyarrhythmia drug. In some examples, the classification is communicated to an external device, such as an IMD programmer or advanced patient management (APM) system. Accurate detection of AF reduces inappropriate delivery of shock therapy, and may help ensure proper device function. For example, accurate detection of AF allows the IMD to correctly perform a mode switch function (e.g., from a DDD pacing mode to a VVI pacing mode) when AF is present.

Figure 6:
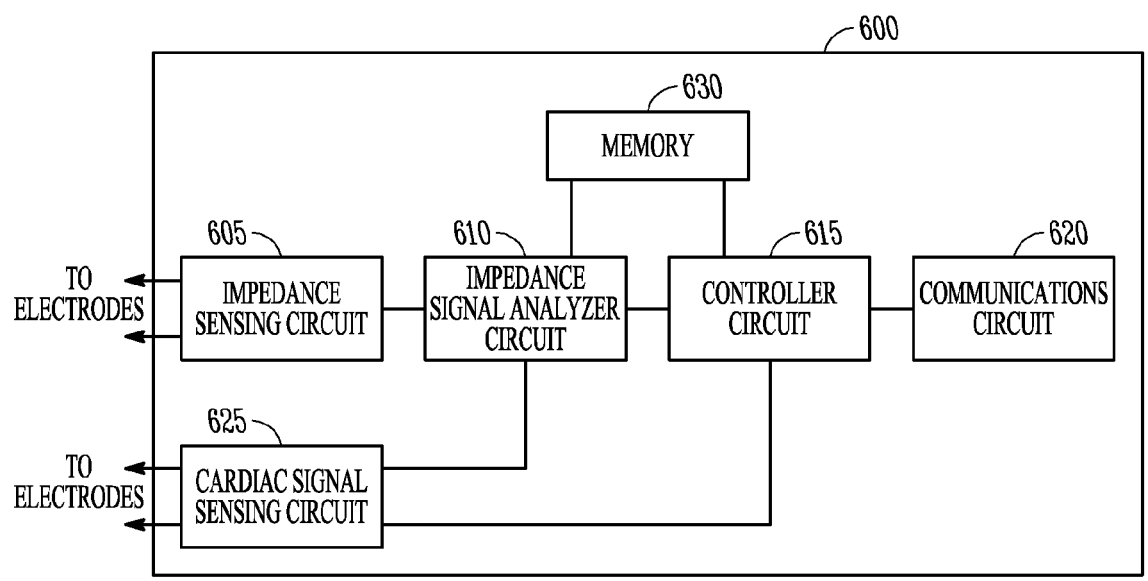
FIG. 6 shows a block diagram of an IMD that detects and classifies atrial tachyarrhythmia.

FIG. 6 shows a block diagram of an IMD 600 that detects and classifies atrial tachyarrhythmia. The IMD 600 includes an impedance sensing circuit 605 configured to sense an atrial impedance signal of a subject when coupled to a plurality of implantable electrodes. In some examples, the electrodes are arranged to provide unipolar sensing of the impedance signal. Because unipolar sensing provides a global atrial impedance signal, differences in atrial chamber wall motion among ST, AT, or AF are evident in the sensed atrial impedance signal.

In AF, the atrial impedance signal sensed with a unipolar vector will have a small peak-to-peak amplitude and will be irregular. The magnitude of the impedance signal (e.g., baseline) will be small due to inefficient emptying and the depolarization rate evident in the signal will be a fast rate. A reentrant tachyarrhythmia such as AT, atrial flutter (AFL), or atrial-ventricular nodal reentrant tachyarrhythmia (AVNRT), will have a more regular atrial wall motion pattern. The atrial impedance signal sensed during a reentrant tachyarrhythmia will have a larger peak-to-peak amplitude and the signal will be more regular. The magnitude of the impedance signal will be larger than AF but still be moderate in value and the depolarization rate will be slower than AF.

ST will have an atrial wall motion pattern that is regular. The depolarization rate evident in the atrial impedance signal will be slower than AF or AT/AFL/AVNRT, the peak-to-peak amplitude will be larger, and the magnitude of the impedance signal will be largest among the categories of atrial tachyarrhythmia.

In some examples, the sensing electrodes coupled to the impedance sensing circuit 605 include an arrangement that provides bipolar sensing of the impedance signal. Because a bipolar sense vector provides a localized intra-atrial impedance signal, differences among the various types of atrial tachyarrhythmia are evident as differences in atrial blood volume change patterns.

The change in blood volume of an atrium is affected by filling of the associated ventricle and by cycles of atrial contraction and relaxation. Therefore, the localized atrial impedance signal may have more than one signal component including one due to the ventricular filling and one due to the atrial contraction/depolarization. When the ventricles are operating normally during an atrial tachyarrhythmia, the ventricular contraction component has a lower frequency and may appear to be a near-DC impedance signal compared to the higher frequency atrial component.

Similar to the unipolar sense vector, in AF, the intra-atrial impedance signal sensed with a bipolar vector will have a small peak-to-peak amplitude due to irregular contractions. A reentrant tachyarrhythmia such as AT/AFL/AVNRT will have a larger peak-to-peak amplitude and the signal will be more regular. ST will have even higher peak-to-peak values due to regular contractions at a rate lower than AF or AT/AFL/AVNRT.

Because the localized intra-atrial impedance signal includes a signal component from the associated ventricle, the intra-atrial impedance signal can be used to detect dual tachyarrhythmia (e.g., AF, AFL, or AT in conjunction with VT). In dual tachyarrhythmia, the low frequency near-DC component of the impedance signal will be reduced in amplitude.

The IMD 600 also includes an impedance signal analyzer circuit 610 communicatively coupled to the implantable impedance sensing circuit 605. The communicative coupling provides for exchange of electrical signals between the impedance sensing circuit 605 and the impedance signal analyzer circuit 610 even though their may be intervening circuitry.

The impedance signal analyzer circuit 610 may include any combination of hardware, firmware, or software. In some examples, the impedance signal analyzer circuit 610 includes a digital signal processor, application specific integrated circuit (ASIC), microprocessor, or other type of processor, interpreting or executing instructions in software or firmware. In some examples, the impedance signal analyzer circuit 610 includes one or more modules to perform the functions described herein. A module may include software, hardware, firmware or any combination thereof. Multiple functions may be performed by one or more modules.

The impedance signal analyzer circuit 610 detects a sudden change in a characteristic of the sensed atrial impedance signal that indicates atrial tachyarrhythmia. The characteristic of the signal may include one or more of the amplitude of the atrial impedance signal, the rate of depolarization as evident in the atrial impedance signal, the variation in the rate of the depolarization in the impedance signal, the regularity of the atrial impedance signal, or the morphology of the atrial impedance signal.

From the detected sudden change, the impedance signal analyzer circuit 610 classifies the atrial tachyarrhythmia indication as ST when the detected sudden change satisfies an ST threshold value of the characteristic, classifies the atrial tachyarrhythmia indication as AT when the detected sudden change satisfies an AT threshold value of the characteristic that is different from the ST threshold value, and classifies the atrial tachyarrhythmia indication as AF when the detected sudden change satisfies an AF threshold value of the characteristic that is different from the ST and AT amplitude threshold values.

The impedance signal analyzer circuit 610 provides the classification to a user or process. In some examples, the impedance signal analyzer circuit 610 is integral to, or communicatively coupled to, a controller circuit 615 that receives the tachyarrhythmia classification. In response, the controller circuit 615 may initiate an anti-tachyarrhythmia treatment such as anti-tachycardia pacing (ATP) or delivery of an anti-tachyarrhythmia drug. In some examples, the IMD 600 includes a communication circuit 620 that communicates wireless signals with an external device, and the classification is communicated to the external device.

As described previously, in some examples the impedance signal analyzer circuit 610 detects atrial tachyarrhythmia by detecting, among other things, a sudden decrease in the amplitude of the sensed atrial impedance signal that is less than a specified amplitude detection threshold value. The impedance signal analyzer circuit 610 classifies the atrial tachyarrhythmia as one of ST, AT, or AF according to the detected amplitude decrease. The change is deemed to be sudden if the change occurs within a specified number of cardiac cycles (e.g., one to three cardiac cycles) or in a specified number of seconds. The period of time that defines a sudden decrease can be programmable.

In some examples, the sudden decrease in amplitude is a decrease in the peak-to-peak amplitude of the atrial impedance signal. In some examples, the sudden decrease in amplitude is a decrease in the baseline-to-peak amplitude of the atrial impedance signal. The baseline can be determined by the impedance signal analyzer circuit 610 through signal processing such as filtering and/or determining a central tendency of the baseline.

In some examples, the impedance signal analyzer circuit 610 calculates a central tendency (e.g., an ensemble average or other average) of the amplitude of the sensed atrial impedance signal, and the sudden change in the amplitude is a sudden change in the amplitude of the determined central tendency of the sensed atrial impedance signal.

According to some examples, the impedance signal analyzer circuit 610 detects atrial tachyarrhythmia by detecting a sudden increase in an atrial depolarization rate that exceeds a specified atrial rate detection threshold value, or conversely, by detecting a sudden decrease in an atrial depolarization interval that is less than a specified atrial depolarization interval detection threshold value.

In some examples, the impedance signal analyzer circuit 610 includes an implantable cardiac signal sensing circuit 625 communicatively coupled to the impedance signal analyzer circuit. The cardiac signal sensing circuit 625 senses a cardiac signal associated with a cardiac action potential signal of the subject when coupled to a plurality of implantable electrodes. The electrodes may be the same or different from the electrodes coupled to the impedance sensing circuit 605.

Cardiac action potentials propagate through the heart's electrical conduction system to excite various regions of myocardial tissue. The cardiac signal sensing circuit 625 provides an electrical signal representative of such signals. Examples of the cardiac signal sensing circuit 625 include, without limitation, a subcutaneous electrocardiogram (ECG) sensing circuit, an intra-cardiac electrogram (EGM) sensing circuit, and a wireless ECG sensing circuit. In a subcutaneous ECG sensing circuit, electrodes are implanted beneath the skin and the ECG signal obtained is referred to as subcutaneous ECG or far-field electrogram. In an intra-cardiac EGM circuit, at least one electrode is placed in or around the heart. A wireless ECG includes a plurality of electrodes to provide differential sensing of cardiac signals to approximate a surface ECG. Descriptions of wireless ECG systems are found in commonly assigned, co-pending U.S. patent application Ser. No. 10/795,126 by McCabe et al., entitled "Wireless ECG in Implantable Devices," filed on Mar. 5, 2004, which is incorporated herein by reference. The impedance signal analyzer circuit 610 detects the sudden change in the atrial depolarization rate or interval using both of the sensed atrial impedance signal and a sensed atrial action potential signal.

In some examples, the impedance signal analyzer circuit 610 detects tachyarrhythmia using the sensed cardiac signal provided by the cardiac signal sensing circuit 625, such as by an assessment of heart rhythm stability when a subject experiences a sudden increase in heart rate. Examples of methods and systems to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

Blending the atrial tachyarrhythmia detection of the cardiac signal sensing circuit 625 and the atrial impedance sensing circuit 605 may improve the detection accuracy of AF or AT. Because the cardiac signal sensing circuit 625 may use electrodes different the detection by the impedance sensing circuit 605, the robustness of the detection system may be improved.

The impedance signal analyzer circuit 610 classifies the detected atrial tachyarrhythmia using the sensed atrial impedance signal and using the sensed cardiac signal provided by the cardiac signal sensing circuit 625. In certain examples, the impedance signal analyzer circuit 610 weights the detection by the cardiac signal sensing circuit 625 differently than the detection by the impedance sensing circuit 605, and classifies the atrial tachyarrhythmia according to the weights. In certain examples, the impedance signal analyzer circuit 610 includes the detection by the cardiac signal sensing circuit 625 and the detection by the impedance sensing circuit 605 in a decision tree and detects and/or classifies the atrial tachyarrhythmia accordingly.

In some examples, the impedance signal analyzer circuit 610 detects atrial tachyarrhythmia by detecting a sudden increase in variation of atrial depolarization rate or interval (A-A interval) measured using the sensed atrial impedance signal. For example, the impedance signal analyzer circuit 610 may monitor A-A intervals as detected in the atrial impedance signal, and calculate a running baseline average of the A-A interval. The impedance signal analyzer circuit 610 may include a peak detector circuit to detect the A-A intervals. The impedance signal analyzer circuit 610 detects a sudden change in the variation when M of N A-A intervals are outside of an A-A interval range of the baseline, where M and N are integers and M is less than N. The interval range, M, and/or N can be specified differently for ST, AT, and AF. The impedance signal analyzer circuit 610 classifies the atrial tachyarrhythmia as one of ST, AT, or AF according to the detected increase in variation.

According to some examples, the IMD 600 includes a memory 630 integral to, or separate from, the impedance signal analyzer circuit 610. The memory 630 stores a template of morphology of an atrial impedance signal. In some examples, the template is representative of the atrial impedance signal during normal sinus rhythm (NSR). For example, a template can be created for a patient using a CFM by providing electrical energy pulses to the supra-ventricular region of the patient's heart. The resulting cardiac complexes are then sensed and used to create a template for use in a morphology-based cardiac signal classification algorithm. Systems and methods of creating templates for a morphology-based algorithm are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference.

The morphological template represents an atrial mechanical activation pattern that is free of AF or AT. Features such as amplitude, A-A interval, etc., can be included in the morphological template. In some examples, the morphological template includes the electrical-mechanical relationship timing between a sensed electrical cardiac signal and the sensed atrial impedance signal. The impedance signal analyzer circuit 610 compares the sensed atrial impedance signal to the stored morphology template, and detects atrial tachyarrhythmia from a sudden change from the stored morphology template. The impedance signal analyzer circuit 610 classifies the detected tachyarrhythmia as one of ST, AT, or AF according to the comparison and to the sudden change in the characteristic.

In some examples, the memory 630 stores a number of historical atrial impedance signal morphology templates and a current atrial impedance morphology template. The templates are indicative of NSR. The impedance signal analyzer circuit 610 compares an atrial impedance signal sensed during NSR to the historical and current morphology templates and declares which morphology template is the current morphology template based on the comparison. The impedance signal analyzer circuit 610 classifies the detected atrial tachyarrhythmia as one of ST, AT, or AF according to a comparison to the declared current morphology template.

In some examples, the memory 630 stores a template for each of NSR, ST, AT, and AF and classifies the rhythm according to comparisons to the stored templates. In certain examples, the impedance signal analyzer circuit 610 calculates a feature correlation coefficient (FCC) from a comparison of the detected rhythm with each of the stored templates and classifies the detected rhythm according to the calculated FCC.

In some examples, the impedance signal analyzer circuit 610 detects a sudden decrease in a measure of regularity of the sensed atrial impedance signal that is less than a regularity measure threshold. In certain examples, the measure of regularity is calculated for the shape of the sensed atrial impedance signal segment. Conversely, the impedance signal analyzer circuit 610 detects a sudden increase in a measure of variability of sensed atrial impedance signal. Examples of a measure of variability include, among other things, a variance of a fiducial representing a feature in the atrial impedance signal or a standard deviation of the fiducial.

According to some examples, the impedance sensing circuit 605 senses both an atrial impedance signal and a separate ventricular impedance signal of the subject when coupled to a plurality of implantable electrodes. Using a different sensing vector may help assess the impact of the detected AT or AF. The impedance signal analyzer circuit 610 detects a sudden change in a characteristic of the sensed ventricular impedance signal that indicates ventricular tachycardia (VT) and detects the sudden change in the atrial impedance signal that indicates atrial tachyarrhythmia. The impedance signal analyzer circuit 610 provides an indication of atrial tachyarrhythmia and ventricular tachyarrhythmia to a user or process.

According to some examples, the impedance sensing circuit 605 senses a combined atrial and ventricular impedance signal of the subject when coupled to the plurality of implantable electrodes. The impedance signal analyzer circuit 610 is configured to remove a ventricular component of the impedance signal to obtain the atrial component. In certain examples, the impedance signal analyzer circuit 610 includes a filter circuit to obtain the atrial component of the signal. The impedance signal analyzer circuit 610 then uses the separated components of the impedance signal to detect and classify the tachyarrhythmia.

The time that a patient spends in AF is sometimes called an AF burden. A device estimate of the AF burden is useful to a physician to determine which anti-arrhythmic therapy or therapies to use, or which anticoagulant therapy or therapies to prescribe. In some examples, the impedance signal analyzer circuit 610 classifies a detected tachyarrhythmia as AF or AT using the atrial impedance signal. When the impedance signal analyzer circuit 610 detects a return to normal atrial impedance after detecting the AF or AT, the time duration of the AF or AT is determined. The impedance signal analyzer circuit 610 calculates the AF or AT burden of the subject using the time duration, and provides the AF or AT burden calculation to a user or process.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable impedance sensing circuit configured to sense an atrial impedance signal of a subject and adapted to be coupled to a plurality of implantable electrodes; and
   an impedance signal analyzer circuit, communicatively coupled to the implantable impedance sensing circuit, configured to:
   detect a sudden change, in a characteristic of the sensed atrial impedance signal, that indicates atrial tachyarrhythmia;
   classify the atrial tachyarrhythmia indication as sinus tachycardia (ST) when the detected sudden change satisfies an ST threshold value of the characteristic;
   classify the atrial tachyarrhythmia indication as atrial tachycardia (AT) when the detected sudden change satisfies an AT threshold value of the characteristic that is different from the ST threshold value;
   classify the atrial tachyarrhythmia indication as atrial fibrillation (AF) when the detected sudden change satisfies an AF threshold value of the characteristic that is different from the ST and AT amplitude threshold values; and
   provide a classification of the tachyarrhythmia to a user or process.

2. The apparatus of claim 1, wherein the impedance signal analyzer circuit is configured to detect a sudden decrease in an amplitude of the sensed atrial impedance signal that is less than an amplitude threshold value, and classify the indication as ST, AT, or AF according to the detected decrease.

3. The apparatus of claim 2, wherein the impedance signal analyzer circuit is configured to detect at least one of:
   a sudden decrease in a calculated central tendency of the amplitude of the sensed atrial impedance signal;
   a sudden decrease in a baseline-to-peak amplitude of the atrial impedance signal; and
   a sudden decrease in a peak-to-peak amplitude of the atrial impedance signal.

4. The apparatus of claim 1, wherein the impedance signal analyzer circuit is configured to detect a sudden change in an atrial depolarization rate or interval in the sensed atrial impedance signal that satisfies a specified rate or interval threshold value.

5. The apparatus of claim 4, including:
   an implantable cardiac signal sensing circuit, communicatively coupled to the impedance signal analyzer circuit, configured to sense a cardiac signal associated with a cardiac action potential signal of the subject when coupled to a plurality of implantable electrodes, and
   wherein the impedance signal analyzer circuit is configured to detect the sudden change in the atrial depolarization rate or interval using both of the sensed atrial impedance signal and a sensed atrial action potential signal.

6. The apparatus of claim 1, wherein the impedance signal analyzer circuit is configured to detect a sudden increase in variation of atrial depolarization rate or interval measured using the sensed atrial impedance signal.

7. The apparatus of claim 1, wherein the impedance signal analyzer circuit is configured to detect a sudden decrease in a measure of regularity of the sensed atrial impedance signal that is less than a regularity measure threshold.

8. The apparatus of claim 1, including a memory, communicatively coupled to the impedance signal analyzer circuit, to store a template of morphology of an atrial impedance signal, and
   wherein the impedance signal analyzer circuit is configured to:
      compare the sensed atrial impedance signal to the stored morphology template;
      detect a change from the stored morphology template; and
      classify the detected tachyarrhythmia as one of ST, AT, or AF according to the comparison and to the sudden change in the characteristic.

9. The apparatus of claim 1, including a memory, communicatively coupled to the impedance signal analyzer circuit, to store a number of historical atrial impedance signal morphology templates and a current atrial impedance morphology template, wherein the templates are indicative of a normal sinus rhythm (NSR), and
   wherein the impedance signal analyzer circuit is configured to:
      compare an atrial impedance signal sensed during NSR to the historical and current morphology templates;
      declare which morphology template is the current morphology template; and
      classify the detected tachyarrhythmia as one of ST, AT, or AF according to a comparison to the declared current morphology template.

10. The apparatus of claim 1, wherein the impedance sensing circuit is configured to sense both the atrial impedance signal and a ventricular impedance signal of the subject, and wherein the impedance signal analyzer circuit is configured to:
   detect a sudden change, in a characteristic of the sensed ventricular impedance signal, that indicates ventricular tachycardia (VT); and
   provide an indication of atrial tachyarrhythmia and ventricular tachyarrhythmia to a user or process.

11. The apparatus of claim 1, wherein the impedance sensing circuit is configured to sense a combined atrial and ventricular impedance signal of the subject, and wherein the impedance signal analyzer circuit is configured to remove a ventricular component of the impedance signal to obtain the atrial component.

12. The apparatus of claim 1, including:
   an implantable cardiac signal sensing circuit configured to sense a cardiac signal associated with a cardiac action potential signal of the subject and adapted to be coupled to a plurality of implantable electrodes, and
   wherein the impedance signal analyzer circuit is configured to classify the detected atrial tachyarrhythmia using the sensed atrial impedance signal and the sensed cardiac signal.

13. The apparatus of claim 1, wherein the impedance signal analyzer circuit is configured to:
   classify the tachyarrhythmia as AF or AT using the atrial impedance signal;
   detect a return to normal atrial impedance after detecting the AF or AT;
   determine a time duration of the AF or AT;
   calculate the AF or AT burden of the subject using the time duration; and
   provide the AF or AT burden calculation to a user or process.

14. The apparatus of claim 1, wherein the implantable impedance sensing circuit is configured to be coupled to an implantable bipolar pair of impedance sensing electrodes and to sense a localized intra-atrial impedance signal using the implantable bipolar pair of impedance sensing electrodes.

15. The apparatus of claim 1, including an implantable housing and an electrode formed on the implantable housing, and wherein the implantable impedance sensing circuit is configured to sense a global atrial impedance signal using the electrode formed on the implantable housing.

16. A method comprising:
   sensing an atrial impedance signal of a subject with an implantable medical device (IMD);
   detecting a sudden change in a characteristic of the sensed atrial impedance signal that indicates atrial tachyarrhythmia;
   classifying the detected atrial tachyarrhythmia as sinus tachycardia (ST) when the sudden change in a characteristic of the atrial impedance signal satisfies an ST threshold value of the characteristic;
   classifying the detected atrial tachyarrhythmia as atrial tachycardia (AT) when the sudden change in the characteristic of the atrial impedance signal satisfies an AT threshold value of the characteristic that is different from the ST threshold value;
   classifying the detected atrial tachyarrhythmia as atrial fibrillation (AF) when the sudden change in the characteristic of the atrial impedance signal satisfies an AF threshold value of the characteristic that is different from the ST and AT amplitude threshold values; and
   providing a classification of the tachyarrhythmia to a user or process.

17. The method of claim 16, wherein detecting a sudden change in a characteristic of the atrial impedance signal includes detecting a sudden decrease in an amplitude of the atrial impedance signal that is less than an amplitude threshold value, and wherein classifying includes classifying the detected tachyarrhythmia as one of ST, AT, or AF according to the sudden decrease in amplitude.

18. The method of claim 16, wherein detecting a sudden change in a characteristic of the atrial impedance signal includes detecting, using the atrial impedance signal, a sudden change in an atrial depolarization rate or interval that exceeds a rate threshold value or is less than a depolarization interval threshold value, and wherein classifying includes classifying the detected tachyarrhythmia as one of ST, AT, or AF according to the sudden change in the atrial depolarization rate or interval.

19. The method of claim 16, wherein detecting the sudden change in a characteristic of the atrial impedance signal includes detecting a sudden decrease in a measure of regularity of the atrial impedance signal that is less than a regularity measure threshold, and wherein classifying includes classifying the detected tachyarrhythmia as one of ST, AT, or AF according to the sudden decrease in the measure of regularity.

20. The method of claim 16, wherein detecting the sudden change in a characteristic of the atrial impedance signal includes detecting a sudden increase in a variation of atrial depolarization rate measured using the atrial impedance signal, and wherein classifying includes classifying the detected tachyarrhythmia as one of ST, AT, or AF according to the sudden increase in the variation.

21. The method of claim 16, including:
 storing a template of morphology of an atrial impedance signal;
 comparing the sensed atrial impedance signal to the stored morphology template, wherein detecting the sudden change in a characteristic of the atrial impedance signal includes detecting a change using the comparison to the stored morphology template; and
 classifying the detected tachyarrhythmia as one of ST, AT, or AF according to the comparison and to the sudden change in the characteristic.

22. The method of claim 21, wherein storing the morphology template of an atrial impedance signal includes:
 storing a number of historical atrial impedance signal morphology templates and a current atrial impedance morphology template, wherein the templates are indicative of a normal sinus rhythm (NSR);
 comparing an atrial impedance signal sensed during NSR to the historical and current morphology templates;
 declaring which morphology template is the current morphology template; and
 classifying the detected tachyarrhythmia as one of ST, AT, or AF according to a comparison to the declared current morphology template.

23. The method of claim 16, including:
 sensing a ventricular impedance signal of the subject with the IMD;
 detecting a sudden change, in a characteristic of the sensed ventricular impedance signal, that indicates ventricular tachycardia (VT); and
 providing an indication of atrial tachyarrhythmia and ventricular tachyarrhythmia to a user or process.

24. The method of claim 16, wherein sensing an atrial impedance signal of a subject includes:
 sensing a combined atrial and ventricular impedance signal; and
 removing a ventricular component of the impedance signal to obtain the atrial component.

25. The method of claim 16, wherein classifying the detected tachyarrhythmia includes classifying the tachyarrhythmia as AF using the atrial impedance signal, and wherein the method includes:
 detecting a return to normal atrial impedance;
 determining a time duration of the AF;
 calculating the AF burden of the subject using the time duration; and
 providing the AF burden calculation to a user or process.

* * * * *